United States Patent [19]
Brown et al.

[11] Patent Number: 5,158,086
[45] Date of Patent: Oct. 27, 1992

[54] INVASIVE PROBE SYSTEM

[75] Inventors: D. Michael Brown, Tempe, Ariz.; Homer Fairley, Dunblane, Scotland

[73] Assignee: W. L. Gore & Associates, Inc., Newark, Del.

[21] Appl. No.: 556,586

[22] Filed: Jul. 20, 1990

[51] Int. Cl.$^5$ .............................................. A61B 8/00
[52] U.S. Cl. .................................. 128/662.03; 128/4
[58] Field of Search ................. 174/36, 111, 115, 103; 128/4, 6, 635, 804, 662.06, 662.03; 606/27, 28

[56] References Cited

U.S. PATENT DOCUMENTS

| | | | |
|---|---|---|---|
| 3,858,586 | 1/1975 | Lessen | 128/4 |
| 4,108,211 | 8/1978 | Tanaka | 128/4 |
| 4,119,102 | 10/1978 | LeVeen | 128/804 |
| 4,207,874 | 6/1980 | Choy | 604/21 |
| 4,440,973 | 4/1984 | Hawkins | 174/111 |
| 4,494,549 | 1/1985 | Namba et al. | 128/662.06 |
| 4,530,568 | 7/1985 | Haduch et al. | 128/6 |
| 4,543,960 | 10/1985 | Harui et al. | 128/662.06 |
| 4,605,009 | 8/1986 | Pourcelot et al. | 128/6 |
| 4,633,882 | 1/1987 | Matsuo et al. | 128/662.06 |
| 4,655,257 | 4/1987 | Iwashita | 128/4 |
| 4,669,172 | 6/1987 | Petruzzi | 128/6 |
| 4,688,555 | 8/1987 | Wardle | 128/4 |
| 4,699,463 | 10/1987 | D'Amelio et al. | 128/4 |
| 4,714,075 | 12/1987 | Krauter et al. | 128/4 |
| 4,748,969 | 6/1988 | Wardle | 128/4 |
| 4,790,294 | 12/1988 | Allred, III et al. | 128/4 |
| 4,834,102 | 5/1989 | Schwarzchild et al. | 128/662.06 |
| 4,877,923 | 10/1989 | Sahakian | 174/115 |
| 4,879,991 | 11/1989 | Ogiu | 128/6 |
| 4,989,581 | 2/1991 | Tamburrino et al. | 128/4 |
| 5,043,530 | 8/1991 | Davies | 174/36 |

FOREIGN PATENT DOCUMENTS

| | | | |
|---|---|---|---|
| 0301288 | 7/1988 | European Pat. Off. | 128/4 |
| 3707787A1 | 3/1987 | Fed. Rep. of Germany | 128/4 |
| 2143920A | 6/1984 | United Kingdom | 128/4 |

OTHER PUBLICATIONS

Article entitled: "Measuring Ultrasonic Velocity in Materials", pp. 251–265.

*Primary Examiner*—Francis Jaworski
*Assistant Examiner*—George Manuel
*Attorney, Agent, or Firm*—Gary A. Samuels

[57] ABSTRACT

An invasive probe system has a hand-held, electrically powered controller acting through a position control cable having a vertebrae-type articulation assembly for connecting to a probe head. The control cable has four control wires in a PTFE multichannel lumen positioned proximate the cable centerline with coaxial signal carriers surrounding the grouped control wires. The articulation assembly includes a plurality of integrally formed vertebrae member units pivotably interconnected by ball and socket snap-fit elements on each unit. Microswitches in the hand-held controller control lead screw-equipped servo motors to actuate rack-type linear drives for the control wires, allowing single hand probe head positioning.

19 Claims, 6 Drawing Sheets

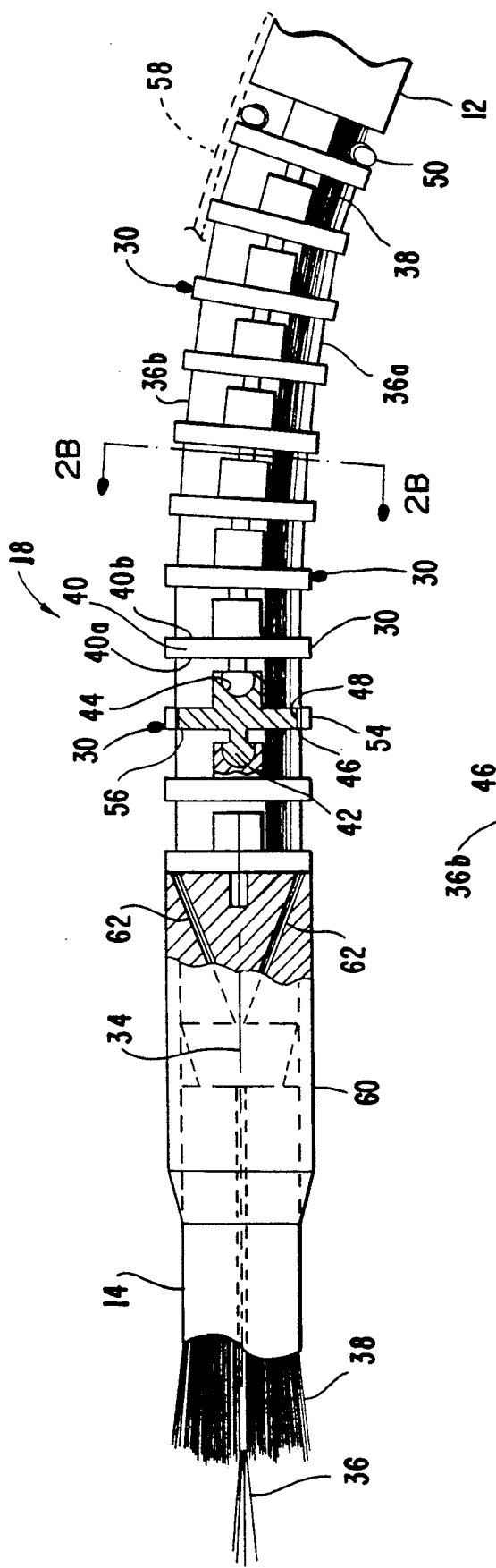

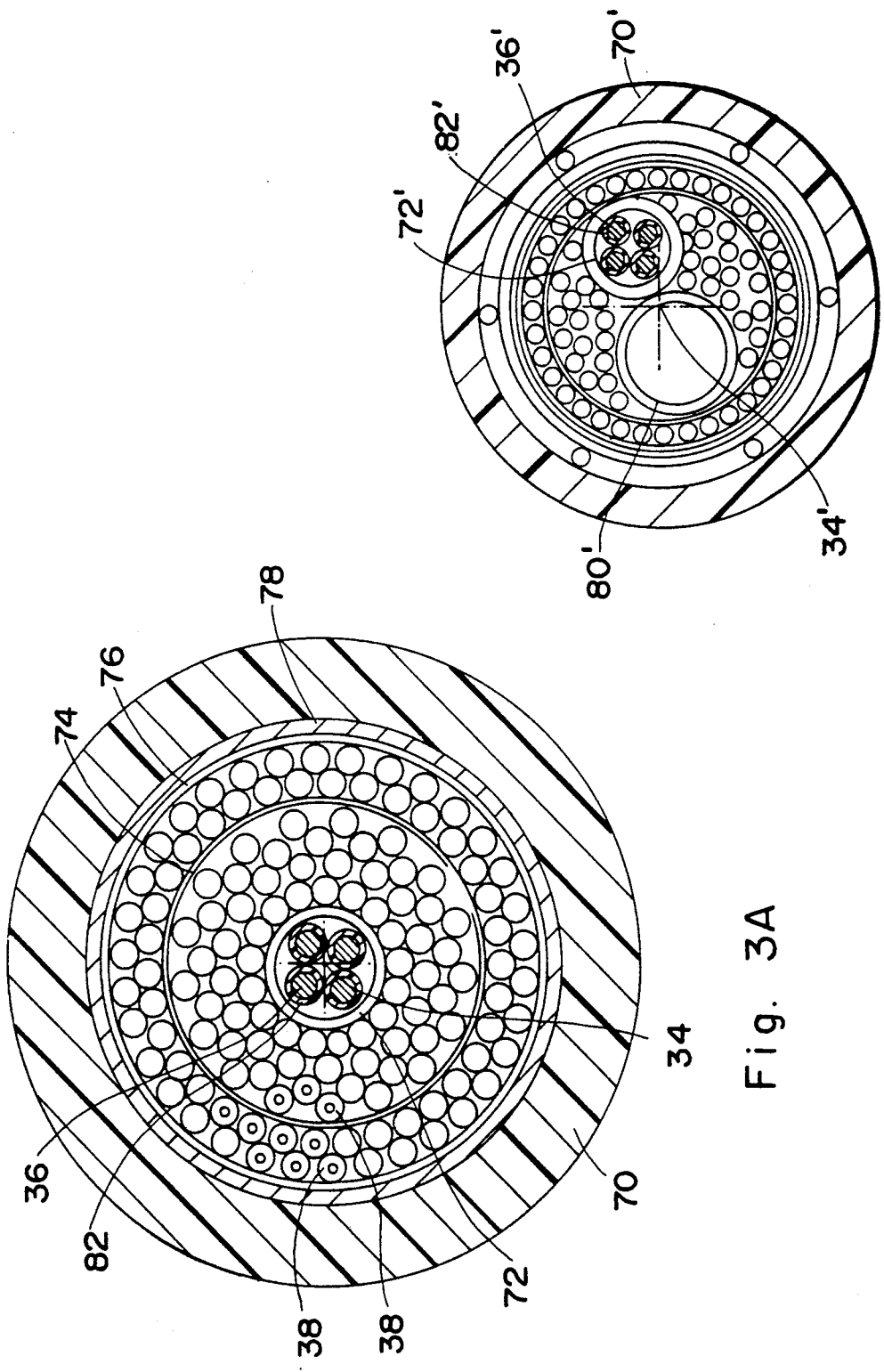

INVASIVE PROBE SYSTEM

BACKGROUND OF THE INVENTION

1. Field of the Invention:

This invention relates to an invasive probe system for use in both industrial and medical applications and, more particularly, to invasive probe systems of the type having a probe head interconnected to a controller by a signal-carrying position control cable having means for articulating the probe head.

2. Description of the Prior Art:

Invasive probe systems of the general type set forth above are known, such as are disclosed e.g. in U.S. Pat. No. 4,748,969 (Wardle), U.S. Pat. No. 4,530,568 (Haduch et al.), U.S. Pat. No. 4,834,102 (Schwarzchild et al.), and U.S. Pat. No. 4,633,882 (Matsuo et al.). The probe heads utilized in such systems uniformly include electronic, optical or acoustical (ultrasonic) imaging devices and thus require a remote position control cable having a signal-carrying capability, with a multichannel capacity being highly preferred for increased resolution. The probe heads also may be configured for effecting treatment of some sort upon correct positioning. The need to image mechanical parts or body organs hidden from view along a probe entry path, or at least in a position oblique to the path, requires the system to be capable of articulating the probe head to some degree relative to the longitudinal probe insertion path.

Conventional systems have attempted to solve the problem of articulation in a variety of ways, including the use of vertebrae-like devices connecting the cable to the probe head and the use of cable structures capable of controlled bending along the cable centerline. These conventional solutions use control wires or sheaths disposed along the control cable usually in conjunction with a frame-like member in the cable to actuate the vertebrae devices while preventing cable deformation, or to provide controlled bending of the cable itself. In either case, the cable frame members can add unacceptably to the cable diameter or restrict the cross-sectional area available for signal-carrying or treatment conduits.

Conventional vertebrae connecting devices generally utilize vertebrae units restricted to two-dimensional motion between any two adjacent units and depend upon connecting pairs being angularly offset, relative to the vertebrae longitudinal axis, to achieve a three-dimensional articulation capability which is highly desirable. Moreover, the pin-type hinge attachment between vertebrae units in conventional devices can also restrict the angular deflection between adjacent units, thereby possibly unduly increasing the number of units required to achieve a desired probe head angular deflection.

Finally, the controllers used in conventional systems typically use hand-driven rotary knobs extending from the controller housing to actuate the control wires to provide the relative longitudinal movement giving rise to the forces which cause the bending in the vertebrae device or the control cable itself. The controllers generally are themselves hand-held, and the knobs can require the use of the other hand for operation thereby restricting the operator's ability to simultaneously adjust other instrumentation, such as the scanning control devices. Also, the conventional controllers use ratchet-type mechanical stops for fixing the probe head position. These can further complicate the operation of the controller and be ineffective to provide fine control of probe head position.

SUMMARY OF THE INVENTION

Hence, it is an object of the present invention to provide an invasive probe system with a control cable that is radially compact, and wherein the cross-sectional space usable for signal-carrying means or other, non-positional control functions is maximized.

It is a further object of the present invention to provide a system having a vertebrae-type apparatus for connecting the probe head to the control cable but having extended three-dimensional motion between adjacent vertebrae units.

And it is yet a further object of the present invention to provide a system with a controller operable using a single hand for both holding and position controlling to a fine degree.

In accordance with the invention, as embodied and broadly described herein the invasive probe system for use with a probe head includes a radially compact probe head position control cable assembly including control cable and articulation means at one cable end for interconnecting to the probe head; and a hand-held, electrically powered controller operatively connected to the other cable end for actuating the articulation means.

Also in accordance with the invention as embodied and broadly described herein, the radially compact signal-carrying position control cable comprises a tubular housing defining the outer diameter of the control cable, the cable having a longitudinal centerline, at least two longitudinally extending control wires grouped together and positioned within the housing proximate the centerline and configured for relative longitudinal movement with respect to each other and the housing, and longitudinal extending signal-carrying means surrounding the grouped control wires and disposed between the housing and the control wires. Means are provided for reducing friction during relative longitudinal movement among the control wires and the signal-carrying means.

Preferably the cable includes an integral, multichannel tube formed from PTFE positioned proximate the cable centerline wherein the control wires are disposed one to a channel. It is further preferred that for a "bite-resistant" construction, the housing be formed of a resiliently deformable material and that the signal-carrying means includes signal carriers insulated with a resiliently deformable insulation.

Further in accordance with the present invention, as embodied and broadly described herein, the articulation apparatus comprises an assembly of vertebrae-like members defining a longitudinal axis. Each of the plurality of connected members has means for pivotably interconnecting to adjacent ones of the connected members, the pivotable interconnecting means being positioned substantially on an axial intension of the cable centerline; first means for radially and angularly spacing the control wires with respect to the axis, the first means affording relative longitudinal motion between the members and each of the spaced control wires; and second means for holding signal-carrying means. Each of the connected members also may be provided with means for preventing substantial rotation about the axis relative to the adjacent connected member.

Preferably, the pivotable interconnecting means includes a ball element and a socket element axially positioned on opposite sides of, and integrally formed with, a disk-shaped body portion the ball element of one connected member being selectively connectable/disconnectable to the respective socket element of the next-adjacent one of the connected members.

It is also preferred that the second means be longitudinal channels angularly spaced about the axis and open at the disk portion periphery, and wherein each of the connected members further includes retaining ring means selectively engageable with the disk portion periphery for radially capturing the signal-carrying means in the channels.

Still further in accordance with the present invention, as embodied and broadly described herein, the hand-held, powered control apparatus comprises a housing configured for gripping in one hand, and control means configured and positioned in the housing for activation by a thumb or finger associated with the gripping hand. A linear motion-actuated drive assembly is mounted in the housing and connected to the control wires, and rotating motor means is positioned in the housing and operatively connected to the control means. Lead screw means interconnecting the drive assembly and the motor means are provided for converting rotary motor motion to linear motion for actuating the drive assembly.

Preferably, the hand-held, powered control apparatus further includes spring means interconnecting each control wire to said drive assembly for taking up slack in the control wires, and means for indicating the relative longitudinal positions of the control wires, and wherein the lead screw means includes means for providing a mechanical stop for the drive assembly during periods of non-activation of the control means.

Additional objects and advantages of the invention will be set forth in part in the description which follows, and in part will be obvious from the description and drawing, or may be learned by practice of the invention. The objects and advantages of the invention may be realized and attained by means of the instrumentalities and combinations particularly pointed out in the appended claims.

BRIEF DESCRIPTION OF THE DRAWING

FIGS. 2A and 2B are schematic longitudinal cross-sectional and end views, respectively, of the vertebrae-type articulation assembly component of the invasive probe system of FIG. 1;

FIG. 3A, 3B and 3C are schematic cross-sectional views of alternative constructions of the position control cable component of the invasive probe system of FIG. 1.

Reference will now be made in detail to the present preferred embodiment of the invention, examples of which are illustrated in the aforesaid accompanying drawing which is to be considered a part of the specification.

DESCRIPTION OF THE PREFERRED EMBODIMENT

Figure 1:
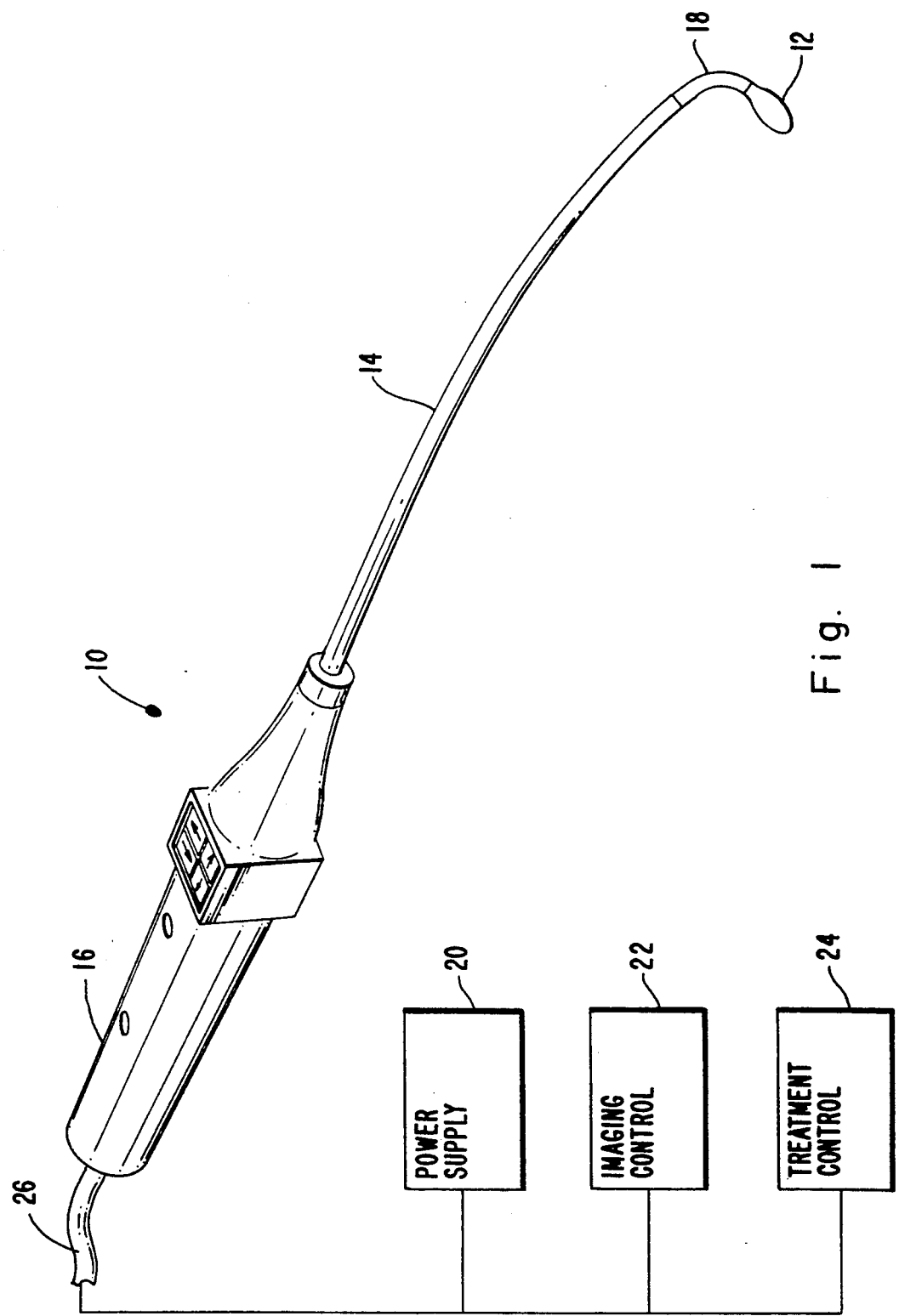
FIG. 1 is a schematic perspective view of an invasive probe system made in accordance with the present invention.

With initial reference to FIG. 1, there is shown a schematic view of an invasive probe system made in accordance with the present invention. The depicted probe system, designated generally by the numeral 10, is especially adapted for medical use as will be apparent from the succeeding explanation. However, the invention is not to be so limited, as other applications including industrial uses will be immediately apparent to those skilled in the art upon reading the present disclosure. Rather, the invention is intended to be limited solely by the appended claims and their equivalents.

In accordance with the present invention, the invasive probe system for use with a probe head includes a probe head position control assembly having a control cable with articulation means at one cable end for connecting the probe head, and a hand-held, electrically powered controller at the other cable end for activating the articulation means through the cable. As embodied herein, FIG. 1 shows invasive probe system 10 for use with probe head 12, including radially compact probe head position control cable 14, hand-held, electrically powered position controller 16, and articulation assembly 18. The positioning of probe head 12 inside a body cavity (or industrial product) is accomplished by activation of articulation assembly 18 by controller 16 through cable 14 by means which will be discussed in greater detail hereinafter.

Probe head 12 which is connected to control cable 14 by articulating means such as articulating assembly 18, can be any of the types known in the art and discussed previously, namely purely imaging or combined imaging-treatment heads. Although not restricted to such use, the present invasive probe system is particularly useful with probe heads of the type using a solid state array of ultrasonic transducers for imaging. The radially compact construction of cable 14 (to be discussed in more detail hereinafter) provides for an increased number a signal carriers for a given cable O.D. or for a reduced O.D for a given number of carriers.

Also depicted schematically in FIG. 1 are power supply 20 for powering hand-held controller 16, imaging controller apparatus 22, and treatment control apparatus 24. Preferably, the connection between controller 16, and each of power supply 20, imaging control apparatus 22, and treatment control apparatus 24 is through a single lead to controller 16, namely lead 26 depicted schematically in FIG. 1, further contributing to the convenience and ease of operation of invasive probe system 10.

Articulation Assembly

In accordance with the present invention, articulation assembly is provided for connecting an invasive probe head to a signal-carrying position control cable of the type having a longitudinal center line, two or more control wires movable relative to one another in the longitudinal direction, and signal carrying means longitudinally disposed alongside the control wires. The articulation assembly specifically includes an assembly of a plurality of connected vertebrae-like members defining a longitudinal axis, the assembly being articulatable along the axis.

As embodied herein and with initial reference to FIG. 2A, the articulation assembly designated generally by the numeral 18 includes several interconnected vertebrae members 30 (ten being shown which, as connected, define longitudinal axis 32. Articulation assembly 18 is connected to cable 14 by means which will be discussed hereinafter such that axis 32 forms an axial extension to cable centerline 34. Cable 14 is of the type having two or more control wires, with the present embodiment utilizing a total of four control wires 36, each being relatively movable with respect to one another and with respect to the other components of cable 14. Cable 14 also includes signal carrying means, in this case a plurality of miniature coaxial cables 38, which are to be interconnected with the sensor or imaging elements in probe head 12.

Further in accordance with the present invention, the articulation assembly of the present invention includes means for pivotably interconnecting adjacent ones of the connected vertebrae members, the pivotal interconnecting means being positioned substantially on the longitudinal axis. As embodied herein, each vertebrae member 30 includes a disk-shaped body portion 40 having opposed axial faces 40a and 40b. Positioned respectively on axial faces 40a and 40b are ball element 42 and socket element 44, with each of ball element 42 and socket element 44 lying substantially on longitudinal axis 32 and being sized to pivotally engage the respective mating element of the next-adjacent vertebrae member. The ball and socket interconnection provides essentially unrestricted articulation about axis 32 and, being located on axis 32, provides a balanced pivot location with no preferred direction of bending. This feature contributes to the ease of operation and accurate positioning of probe head 12.

Further in accordance with the present invention, the articulation assembly also include first means for radially and angularly spacing the control wires with respect to the axis, with the first means affording relative longitudinal motion between the vertebrae members and each of the spaced control wires. As embodied herein, each vertebrae member 30 includes longitudinal extending apertures 46 formed in the outer peripheral portion of the vertebrae member adjacent peripheral edge 48 of disk portion 40. Apertures 46 are angularly spaced about axis 32 and are also radially spaced from axis 32. Apertures 46 are each sized to accommodate relative movement of a single control wire 36. Control wires 36 which are free to slide longitudinally with respect to vertebrae member 30 can be attached directly to probe head 12 or, as shown in FIG. 2A, terminated e.g. by swage fittings 50 after the last-in-line vertebrae member 30. Relative motion between the control wires, such as the leftward movement of control wire 36a relative to control wire 36b in the FIG. 2A schematic, will cause between adjacent vertebrae members 30 and, in the case of the FIG. 2A depiction, downward bending of probe head 12 relative to centerline 34 of cable 14.

Further in accordance with the present invention, the articulation assembly also includes means for holding the signal-carrying means adjacent the longitudinal axis. As embodied herein and with continued reference to FIGS. 2A and 2B, holding means includes channels 52 formed in disk portion 40 and extending radially inward to a position proximate longitudinal axis 32. Four channels 52 are shown (only one with coaxial cables, for clarity), with coaxial cables 38 being ordinarily substantially evenly divided between the four channels to prevent angular differences in the stiffness imparted to articulating assembly 18 by the signal-carriers. Channels 52 are made sufficiently large to permit relative movement between coaxial cables 38 and vertebrae body 40, and thus to minimize sliding interference.

It is highly advantageous during assembly of articulation assembly 18 to have channels 52 open at the peripheral edge surface 48 and to capture the arrayed signal carriers (coaxial cables 38) with a separate retaining ring, such as ring 54. Ring 54 can be configured to snap-connect to peripheral surface 48 of vertebrae member 30 which can have a peripheral groove, such as groove 56, or similar construction to seat ring 54. If articulating assembly 18 is further enclosed by a protective sheath, such as sheath 58 shown dotted in FIG. 2A, it may be possible to eliminate retainer ring 54, particularly if sheath 58 has sufficient resiliency to hold signal carriers in channels 52 during articulation. As seen in FIGS. 2A and 2B, longitudinal apertures 46 for holding control wires 36 also can be open at peripheral surface edge 48 allowing control wires to be captured by ring 54 and possibly affording easier fabrication. However, sheath 58 may not be sufficient to hold control wires 36 in place for large deflections without retainer ring 54, due to the forces tending to displace control wires radially outwardly at the inside of a bend.

As embodied herein, transition member 60 is optionally provided for use with position control cables 14 made in accordance with the present invention which have the control wires normally grouped proximate the cable centerline 34 (see infra.) Transition member 60 is shown rigidly attached to the left-most of vertebrae member 30 and includes four conduits 62 (only two of four conduits shown), one for each control wire 36. Conduits 62 provide a smooth transition from the centerline-proximate position of control wires 36 in cable 14 to the axial-distant spacing in articulating assembly 18. Transition member 60 also can include conduits (not shown) for grouping multielement signal-carrying means such as coaxial cables 38 in the preferred embodiment. The right-most vertebrae member 30 in FIG. 2A can be rigidly attached to probe head 12 using mechanical fasteners (not shown) or equivalent means.

The preferred embodiment of the individual vertical member 30 units of articulation assembly 18 as shown in FIGS. 2A and 2B has disk portion 40 and ball and socket elements 42 and 44 all integrally formed. A resilient plastic such as an acetal copolymer e.g. Celcon made by Celanese or an injection moldable polyamide such as Nylon can be utilized such that vertebrae member 30 has sufficient strength to retain structural integrity against the forces imposed by control wires 36 and also to allow socket element 44 to be sized for a snap-fit interconnection with ball element 42 of the adjacent vertebrae member unit. This provides further convenience and ease of assembly and disassembly, including replacement of worn out units, etc. Retaining ring 54 also can be made of a similar resilient plastic.

Further, as can be discerned from FIG. 2A, the maximum degree of articulation (bending) between adjacent vertebrae member 30 is determined in the depicted embodiment by interference between the disk portion 40 and the socket element 44 of adjacent units. Hence, the maximum degree of articulation can be controlled by offsetting ball element 42 from the respective axial face of disk portion 40 to achieve a greater or lesser degree of articulation between adjacent units. Of course, one skilled in the art would realize that alternate constructions are possible such as where articulation-limiting interference between the peripheral edge portions of adjacent vertebrae member 30 units occurs, and that variations in the degree of articulation between adjacent units in such a construction can be achieved by varying the offset of either or both the socket element 44 or the ball element 42. Such alternate constructions are intended to come within the scope of the appended claims.

During operation of the articulation assembly 18 of the present invention, some torque-type force may arise which would tend to cause rotation about axis 32 of the individual vertebrae members 30 relative to one another. Generally, the grouped signal carriers, such as coaxial cable 36, fitted in channel 52 will prevent undue amounts of rotation. However, it may be preferred to incorporate into the vertebrae members additional means to prevent such rotation about axis 32.

Figure 2D:
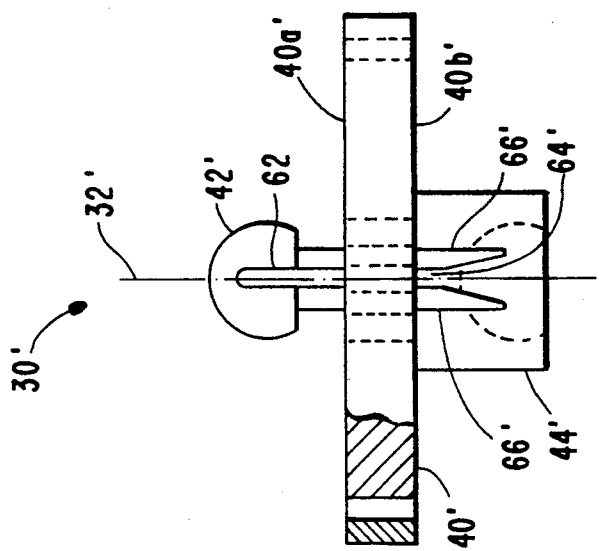
FIGS. 2C and 2D are partial cross-sectional views, respectively, of an alternate construction for the vertebrae articulation assembly.
Figure 2C:
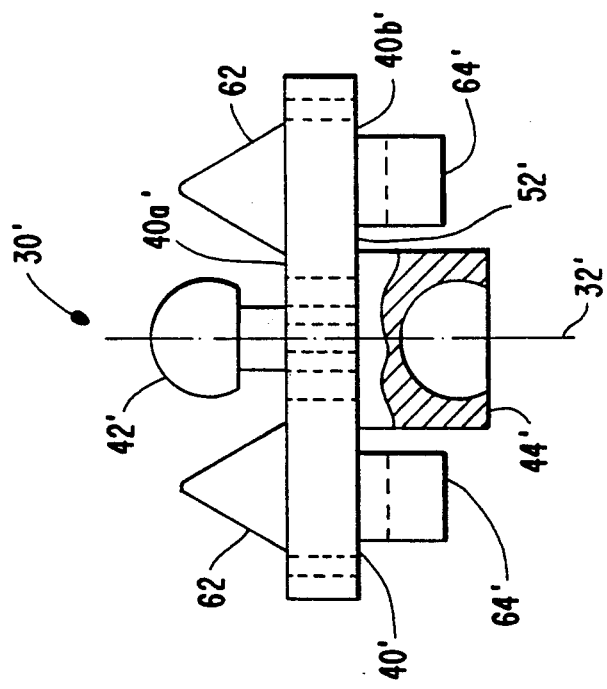

As further embodied herein, and with reference to FIGS. 2C and 2D showing an alternative vertebrae member construction (designated generally as 30') having a disk portion 40', with opposing axial faces 40a' and 40b' having ball element 42' and socket element 44', respectively, located on axis 32'. In this depicted alternative construction, anti-rotation means are provided including longitudinally extending pin elements 62' spaced about axis 32', from face 40a' and complementary slots 64' in face 40b' for receiving respective pin elements. Slots 64' are sized to loosely receive pin elements 62' to enable assembly 18' to bend without binding. Also, pin elements 62' are sized to be commensurate with the maximum degree of bending between adjacent vertebrae members 30' without disengagement from the respective slot 64'. In vertebrae member 30' pictured in FIGS. 2C and 2D, shoulders 66' are provided on axial face 40b' to extend the axial depth of slots 64' to accommodate the increased degree of bending afforded by the present invention. Although two, diametrically opposed pin elements/slots are depicted a fewer or greater number can be utilized depending upon the particular construction of vertebrae member 30', such as the number and placement of channels 52' for the grouped signal carriers, as would be understood by one skilled in the art.

Position Control Cable

Further in accordance with the present invention, a radially compact signal-carrying position control cable is provided, which cable includes a tubular housing defining the outer diameter of the control cable, at least two longitudinally extending control wires grouped together and positioned within the housing proximate the cable center line, and longitudinally extending signal-carrying means surrounding the grouped control wires and disposed between the housing and the control wires. As embodied herein and with initial reference to FIG. 3A, position control cable 14 includes an outer jacket 70 which serves as the cable housing, that is, defines the outer diameter of the cable and also defines the longitudinal cable centerline 34. Jacket housing 70 can be formed of any of a variety of plastic materials and is relatively thin and flexible, with the depicted cable jacket housing being pressure extruded polyurethane having a 0.050 inch wall thickness and an O.D. of about 0.350 inches. In contrast to some conventional control cables, the thickness of cable housing 70 need only be sufficient to contain and protect the signal carrying means to be discussed infra and need not have an increased thickness necessary to constitute a frame-like member.

Positioned adjacent to and surrounding cable centerline 34 are four control wires 36 which are movable longitudinally with respect to one another and to the housing 70 by means such as controller 16 to be discussed infra. The significance of the central positioning of control wires 36 is that it eliminates entirely the need for a separate frame or other structure such as a thickened housing for supporting wires 36 against inwardly (toward the centerline) directed forces which occur during utilization of the cable. While control wires 36 should be positioned closely adjacent to centerline 34, they need not surround the center line. FIG. 3B shows an alternative embodiment having housing 70', centerline 34, with control wires 36' slightly offset from the centerline to accommodate an oversized treatment conduit 80'. However, significant departures from the center line positioning of control wires 36 can lead to cable distortion due to bending forces arising during operation of the probe system.

Disposed between jacket housing 70 and control wires 36 are signal carrying means including a plurality of individual, miniature coaxial cables 38 (a total of 136 miniature cables for the construction depicted in FIG. 3A). Coaxial cables 38 are closely stacked into two concentric regions defined by respective thin tubes or sleeves 72, 74 and 76. A braided metal shield 78 is positioned between sleeve 76 and jacket housing 70 to minimize externally incident electrical interference. Essentially, jacket housing 70 is spaced from the control wires entirely by the signal-carrying means including cables 38, that is, without the need for non-functional rigid spacer elements, thereby contributing to a radially compact construction. In the depicted embodiment, the coaxial cables each have an 0.016 inch O.D. and use Gortex ® expanded PTFE insulation to achieve 50 ohm electrical performance with a minimum insulation wall thickness, thereby further contributing to the compactness of control cable 14. As well known in the cable production art, PTFE (polytetrafluoroethylene) is an insulative material having lubricant characteristics, and is available in a variety of different forms. Each coaxial cable further includes AWG 40 silverplate or copper alloy center conductor and drain wire, and an aluminized polyester shield. Such coaxial cables are available from W. L. Gore & Associates, Inc.

Figure 3C:
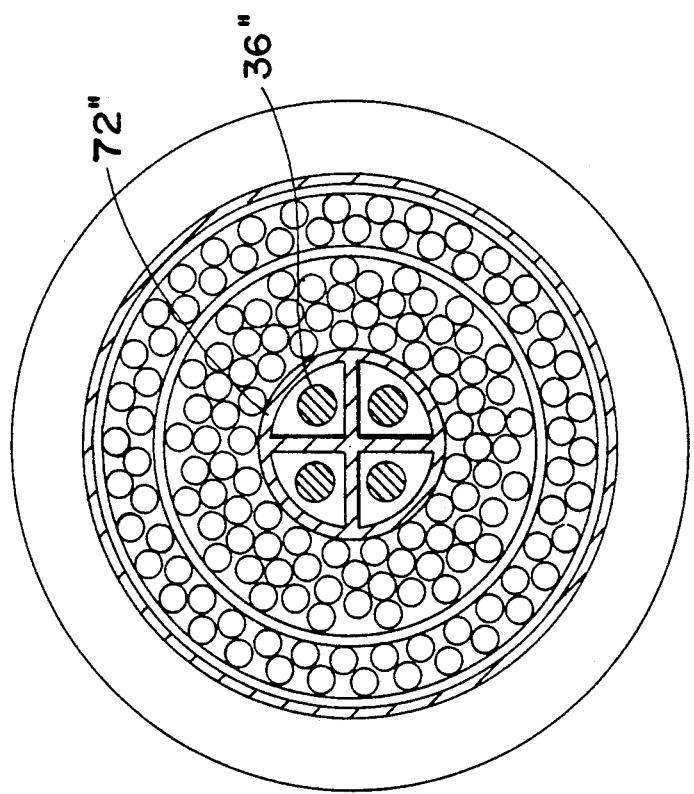

Further in accordance with the present invention, the radially compact control cable includes means for reducing friction during relative longitudinal movement among the control wires and the signal-carrying means. As embodied herein and with reference to FIGS. 3A and 3B, each of guide wires 36 is provided with PTFE coating 82 to minimize friction between the wires. Additionally, tube 72 can be made of PTFE to provide increased protection against friction between control wires 36 and coaxial cables 38. FIG. 3C shows an alternate embodiment wherein tube 72" is multichanneled with one channel per control wire, and formed from extruded PTFE. This latter construction, while more complex, may eliminate the need for PTFE coatings 82 on control wires 36 and thus may be preferred in some applications.

Positioning the control wires proximate the cable centerline as described above advantageously provides a construction that can be made "bite resistant" allowing use with transesopheagal probe heads. Not uncommon occurrences during the use of such probes are involuntary hard biting on the cable by the patient such as accompanying a gagging reflex. The biting can damage conventional control cables which have control wires positioned adjacent the cable outer surface, such as by a frame, and render the cable inoperable.

In accordance with the present invention, the bite-resistant, radially compact cable includes, in addition to the centrally positioned control wires, a housing jacket formed from a resiliently deformable material. Positioned between the control wires and the jacket housing are signal-carrying means including a plurality of signal-carrier members separated from one another by insulation which, like the jacket, is resiliently deformable, but may or may not be of the same material. As embodied herein, the cable 14 described above and depicted in FIG. 3A having a polyurethane jacket 70 and Gortex ® expanded PTFE insulated coaxial cables 36 satisfies the aforementioned requirements. The term "resiliently deformable" is not intended to signify materials which are essentially elastic, but the term also includes materials such as Goretex ® expanded PTFE which can be made to substantially recover to original shape by flexing or other movement following deformation. Consequently, the present bite-resistant cable invention is not intended to be limited to the construction and materials described above which are intended only as an example.

Hand-Held Powered Controller

In accordance with the present invention, a hand-held, powered controller apparatus is provided for controlling the invasive probe head of the type supported and positioned by a control cable having at least two control wires movable longitudinally relative to each other. Specifically, the apparatus includes a housing configured for gripping in one hand and control means configured and positioned in the housing for activation by a thumb or finger associated with the gripping hand. As embodied herein and with reference to FIGS. 4A and 4B, controller 16 includes a generally cylindrical housing 90 dimensioned to comfortably fit in a human hand. Housing 90 is sealed except for suitable openings at housing end 92, for operative attachment of position control cable 14, and at housing end 94, for attachment to lead 26 carrying the power, signal cables and possible treatment conduits as discussed previously. Housing 90 can be of a clam-shell construction and formed from any of a variety of known structural plastic materials such as ABS polycarbonate.

Positioned in housing 90 proximate housing end 92 is an array 96 of microswitches 98. In the preferred embodiment, four microswitches are provided, one for each cartesian direction orthogonal to center line 34 of control cable 14. Array 96 is positioned so that, with housing 90 being held in the operator's hand, switches 98 can be actuated by either the thumb or finger of the gripping hand, thus freeing the other hand for control of imaging, treatment or other equipment.

Further in accordance with the present invention, the hand-held controller apparatus includes a linear motion-actuated drive assembly mounted in the housing and connected to the control wires. As embodied herein, controller 16 includes linear drive assembly 100 which has four linear rack members 102 (only two being shown in FIGS. 4A and 4B) each connected to a respective one of the four control wires 36 of cable 14 by spring means 104 (to be discussed in more detail, infra). The rack members 102 are arranged in two opposed pairs in housing 90, each pair interconnected by a slaved spur gear 106 for mutually dependent, opposite sense linear motion. The cables 36 connected to each interconnected rack members are those diametrically opposed in the articulation assembly 18, e.g., cables 36a and 36b in FIGS. 2A and 2B. Articulation of assembly 18 in a given direction (e.g., downward in the plane of the paper in FIG. 2A) can be accomplished by opposite sense linear motion of the respective control wires 36a and 36b, as will be appreciated by one skilled in the art.

Still in accordance with the present invention, the hand-held, powered controller also includes rotating motor means positioned in the housing and operatively connected to the control means and lead screw means interconnecting the drive assembly and the motor means for converting rotary motor motion to linear motion for actuating the drive assembly. As embodied herein, with reference to FIGS. 4A and 4B, two reversible servo motors 108 (only one being shown in the figures) are positioned in housing 90, and each is interconnected by a lead screw 110 to one of the rack members 102 of a respective rack member pair. Servo motors 108 are electrically interconnected to microswitches 98 such that two opposite direction switches interconnect with the same motor 108, one switch causing forward rotation of the motor, the other reverse rotation. For example, the two microswitches 98 shown in FIGS. 4A and 4B would connect to the same servo motor 108.

Lead screw 110 which converts the rotary motion of motor 108 to the linear motion required to drive racks 102 is selected to have as small a pitch as practicable to allow fine adjustments to be made in the linear position of rack members 102 without unduly lengthening the time to change a probe head position. Also, the small pitch value ensures that lead screw 110 acts as a mechanical stop to prevent movement of rack member 102 (and thus control wires 36 and probe head 12) during periods when microswitches 98 ar not activated. For the above depicted preferred embodiment a 12 volt servo gear motor operating at 44-128 rpm used in conjunction with a lead screw having a pitch of 32/inch was determined to be acceptable.

As further embodied herein, hand-held, powered controller 16 can include a protective sheath 112 disposed within housing 90 and substantially surrounding linear drive assembly 100, motors 108, and lead screw 110. The signal carrying means, in this case coaxial cables 38, are disposed between sheath 112 and housing 90. Controller 16 also can include probe head position indicator means, such as the position indicators depicted schematically as 114 in FIGS. 4A and 4B. Display 114 can be mechanically or electrically activated by the rack members to give an indication of control wire position and thus probe head deflection, e.g. an indicator light display activated by LED position sensors (not shown) connected to rack members 108.

Figure 4A:
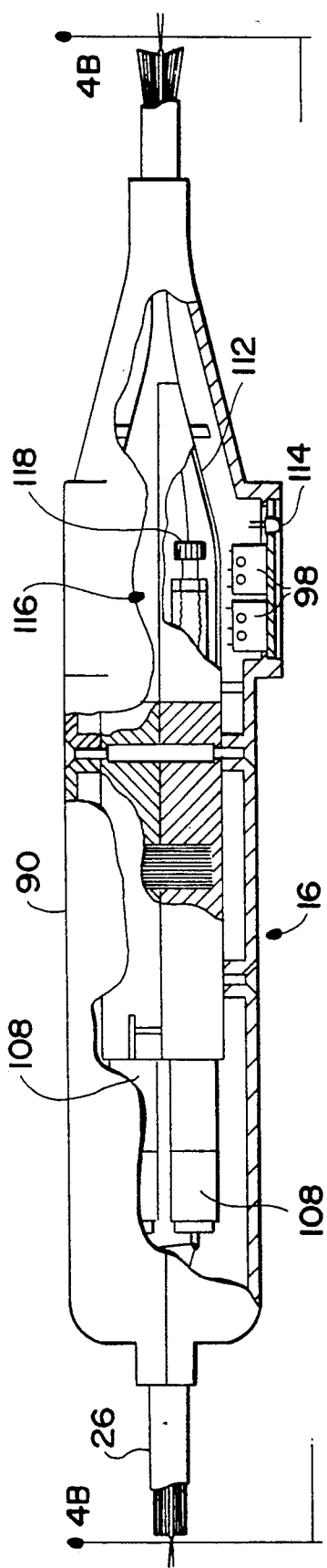
FIGS. 4A and 4B are schematic partial longitudinal cross-sectional views of the hand-held, powered controller component of the invasive probe system of FIG. 1.
Figure 4B:
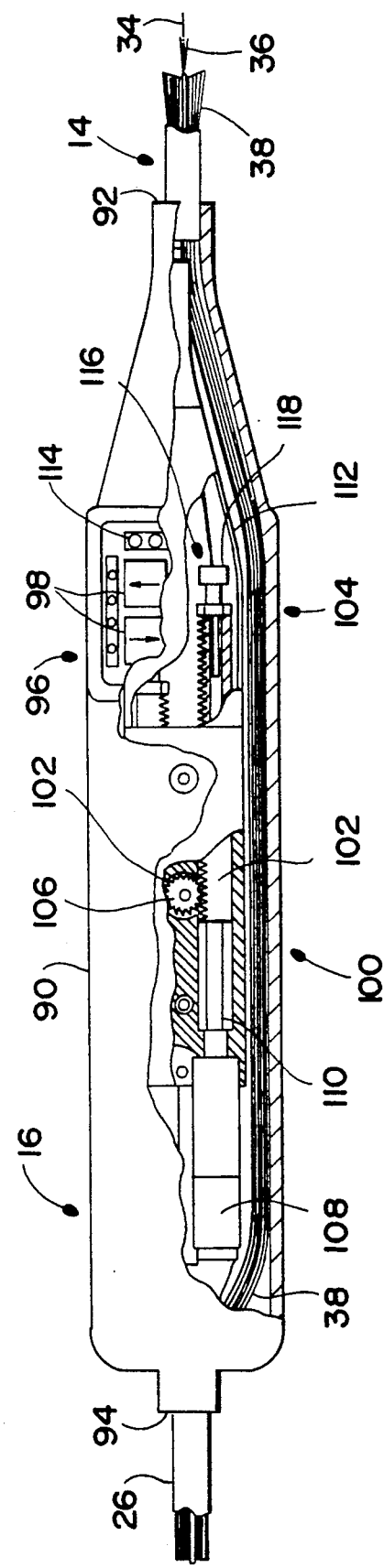

As still further embodied herein, hand-held powered controller 16 includes spring means for interconnecting individual rack members 102 to their respective control wires 36 for adjusting wire tension and accommodating changes in the relative accurate lengths of control wires positioned on the inside and outside of a bend generated in articulation member 18, as will be appreciated by one skilled in the art. FIGS. 4A and 4B depict spring means 116 schematically, and any of several types of tensioning devices such as Belville washer type, and flat-coil type springs can be used together with appropriate connectors, such as take-up screw 118 pictured in FIGS. 4A and 4B.

It will be apparent to those skilled in the art that various modifications and variations could be made in the articulating assembly, the position control cables, and the handheld controllers of the present invasive probe system invention without departing from the scope or spirit of the invention.

What is claimed is:

1. A radially compact signal-carrying position control cable for an invasive probe head, the cable comprising:
   a. a tubular housing defining the outer diameter of the control cable, the cable having a longitudinal centerline;
   b. at least two longitudinally extending control wires grouped together and positioned within said housing proximate said centerline and configured for relative longitudinal movement with respect to each other and said housing;
   c. longitudinal extending signal-carrying means surrounding said grouped control wires and disposed between said housing and said control wires; and
   d. means for reducing friction during relative longitudinal movement between said control wires and said signal-carrying means.

2. The radially compact control cable as in claim 1, said friction reducing means including a dry lubricant coating on said control wires.

3. The radially compact control cable as in claim 2, said coating being PTFE.

4. The radially compact control cable as in claim 1, said friction reducing means including at least one tube formed from a low friction material, said control wires being disposed in said tube.

5. The radially compact cable as in claim 4, said at least one tube being an integral, multi-channel structure formed from PTFE and said control wires being disposed one to a channel.

6. The radially compact control cable as in claim 1, said signal-carrying means including a plurality of radially compact coaxial cables for carrying electrical signals.

7. The radially compact cable as in claim 6, said coaxial cables having expanded PTFE insulation.

8. The radially compact cable as in claim 1, said housing being a multi-layer structure and wherein said signal-carrying means includes means for carrying electrical signals, said housing including means for shielding said electrical signal-carrying means from externally incident electrical interference.

9. The radially compact cable, as in claim 8, said shielding means comprising a braided-wire layer.

10. A bite-resistant, radially compact signal-carrying position control cable for an invasive probe head, the cable comprising:
    a. a tubular housing defining the outer diameter of the control cable, the cable having a longitudinal centerline, said housing being formed of a first resiliently deformable material;
    b. longitudinally extending control wires means positioned within said housing proximate said centerline; and
    c. longitudinal extending signal-carrying means disposed between said housing and said control wire means, said signal-carrying means including a plurality of signal carrier members separated from one another by insulation, said insulation being formed of a second resiliently deformable material.

11. The bite-resistant, radially compact control cable as in claim 10, said first resiliently deformable material being polyurethane.

12. The bite-resistant, radially compact control cable as in claim 10, said second resiliently deformable material being PTFE.

13. The bite-resistant, radially compact cable as in claim 10, said control wire means including a plurality of grouped control wires, and said cable further including a friction-reducing tube member, said tube member being an integral, multi-channel member formed from PTFE, and said control wires being disposed one to a channel.

14. The bite-resistant, radially compact control cable as in claim 10, said signal-carrying means including a plurality of radially compact coaxial cables for carrying electrical signals, and said coaxial cables having expanded PTFE insulation.

15. The bite-resistant, radially compact cable as in claim 10, said signal-carrying means including means for carrying electrical signals, the cable further including resiliently deformable means for shielding said electrical signal-carrying means from externally incident electrical interference.

16. The bite-resistant, radially compact cable as in claim 15, said shielding means comprising a resiliently deformable braided-wire layer positioned between said housing and said signal-carrying means.

17. A hand-held system for supporting an invasive probe head comprising:

a probe head position control cable assembly including a position control cable having a longitudinal centerline and opposing ends, articulation means at one of said opposing cable ends adapted for interconnecting to the probe head, and at least two control wires positioned proximate said centerline, said at least two control wires being operatively connected to said articulation means; and a hand-held, electrically powered controller operatively connected to the other of said opposing cable ends for effecting relative movement of said at least two control wires for actuating said articulation means through said control cable, said controller including control means operable by the thumb or finger of the hand holding said controller.

18. The hand-held invasive probe system as in claim 17 for use with a probe head having a plurality of sensing elements, said position control cable including a plurality of signal carrying means adapted to be operatively connected to said sensing elements and positioned in said control cable to surround said control wires.

19. The invasive probe system as in claim 17, said articulation means including an assembly having a longitudinal axis and a plurality of vertebrae-like elements pivotably interconnected substantially on said longitudinal axis.

* * * * *